United States Patent [19]

Moszner et al.

[11] Patent Number: 6,034,151
[45] Date of Patent: Mar. 7, 2000

[54] HYDROLYZABLE AND POLYMERIZABLE VINYLCYCLOPROPANE SILANES

[75] Inventors: Norbert Moszner, Eschen, Liechtenstein; Thomas Voelkel, Lindau, Germany; Frank Zeuner, Vaduz, Liechtenstein; Sabine Stein, Nenzing, Austria; Volker Rheinberger, Vaduz, Liechtenstein

[73] Assignee: Ivoclar AG, Liechtenstein

[21] Appl. No.: 09/047,592

[22] Filed: Mar. 25, 1998

Related U.S. Application Data

[60] Provisional application No. 60/052,605, Jul. 15, 1997.

[30] Foreign Application Priority Data

Mar. 25, 1997 [DE] Germany .................. 194 14 320

[51] Int. Cl.[7] .................................................. A61K 6/093
[52] U.S. Cl. .................. 523/109; 522/172; 522/908; 526/279; 528/32; 556/465; 556/478
[58] Field of Search .................. 526/279; 523/109; 522/172, 908; 528/32; 556/465, 478

[56] References Cited

U.S. PATENT DOCUMENTS 5,889,132  3/1999  Rheinberger et al. .................. 526/279

*Primary Examiner*—Robert Dawson
*Assistant Examiner*—Jeffrey B. Robertson
*Attorney, Agent, or Firm*—Nixon Peabody LLP

[57] ABSTRACT

Polymerizable and hydrolyzable vinylcyclopropane silanes and in particular silicic acid condensates which can be prepared therefrom are described, which exhibit only a low volume shrinkage on polymerization and produce polymers with high mechanical strength and therefore can be used above all as dental material or a constituent thereof.

20 Claims, No Drawings

HYDROLYZABLE AND POLYMERIZABLE VINYLCYCLOPROPANE SILANES

This application claims the benefit under 35 USC 119(e) of U.S. provisional application, Ser. No. 60/052,605, filed on Jul. 15, 1997.

The invention relates to hydrolysable and polymerizable vinylcyclopropane silanes, processes for the preparation thereof, silicic acid condensates, polymers and compositions prepared therefrom and the use of all these materials inter alia for the preparation of macromolecular compositions and for the preparation of composite materials, adhesives, coatings and in particular dental materials.

Hydrolysable silanes, which contain polymerizable organic radicals, are used in the preparation of coatings, particulate fillers, adhesive compositions and monolithic moulded articles and in the surface modification of reinforcing substances. The silanes are hydrolytically condensed and polymerized thermally, photochemically or by redox initiation, i.e. cured, alone, mixed with other silanes or in the presence of other metal alkoxides.

Of particular interest in connection with the preparation of organic-inorganic composite materials are above all organically modified silanes with polymerizable organic groups, such as vinyl, (meth)acrylic, allyl or styryl groups, since they permit the simultaneous or consecutive formation both of an inorganic and of an organic network and therefore of composite materials with customized properties (cf H. Schmidt, Mat. Res. Soc. Symp. Proc. Vol. 32 (1984), 327–335; H. Schmidt, H. Wolter, J. Non-Cryst. Solids 121 (1990) 428–435). The polymerizable silanes are as a rule initially hydrolytically condensed in solution. After the addition of thermal initiator or photoinitiator and removal of the solvent, nanoparticulate resins then form which are shaped and then polymerized and thus cured.

A major disadvantage of these materials, however, is that the development of the organic network which takes place on polymerization is mostly accompanied by a considerable volume contraction which may result in deformation of the moulded articles, reduction in substrate adhesion, layer separation, development of voids or development of material stresses. A reduced volume contraction takes place with silanes which bear ring-opening groups. In this connection, EP-B-0 358 011 describes scratch-resistant materials inter alia based on 3-glycidyloxypropyl silanes, EP-B-0 486 469 describes organic-inorganic hybrid polymers of 3-glycidyloxypropyl silanes and DE-C-41 33 494 describes dental resin compositions in which e.g. silanes with ring-opening spiroorthoester groups are used. It proves to be disadvantageous, however, that a ring opening is only possible cationically in the case of silanes having epoxide or spiroorthoester groups and these silanes thus polymerize only in the absence of moisture, furthermore the polymerization of the epoxide silanes proceeds sufficiently quickly at elevated temperatures only and the spiroorthoester silanes exhibit only a low stability.

Furthermore,, only trimethylsiloxy-substituted vinylcyclopropanes (cf J. Amer. Chem. Soc. 116 (1994), 6453–6454) and 1-trialkylsilyl-2-vinylcyclopropanes (M. Katsukiyo et al. Tetrahedron Lett. 30 (1989), 4413–4416) have become known up to now as silicon-containing vinylcyclopropane derivatives, i.e. compounds of the following formula:

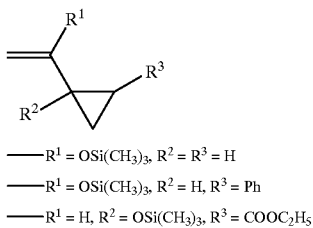

—— $R^1 = OSi(CH_3)_3$, $R^2 = R^3 = H$
—— $R^1 = OSi(CH_3)_3$, $R^2 = H$, $R^3 = Ph$
—— $R^1 = H$, $R^2 = OSi(CH_3)_3$, $R^3 = COOC_2H_5$

It is the object of the invention to provide hydrolysable and polymerizable vinylcyclopropane silanes from which, alone or together with other hydrolytically condensable and polymerizable components, compositions can be prepared which polymerize with only low shrinkage and which are suitable as composite or coating material, adhesive, adhesion promoter or for the preparation of fillers or materials for medical or dental purposes. These silanes are to be able to be covalently incorporated into organic-inorganic composite materials and be synthetically obtainable so that the distance between silicon and the polymerizable groups can be varied.

This object is achieved according to the invention by the hydrolysable and polymerizable vinylcyclopropane silanes according to claims 1 to 3. The invention further relates to the silicic acid condensates according to claim 4, the polymers according to claim 5, the compositions according to claims 6 and 7 and the use according to claim 8.

The hydrolysable and polymerizable vinylcyclopropane silanes according to the invention and the stereoisomers thereof correspond to the general formula (I):

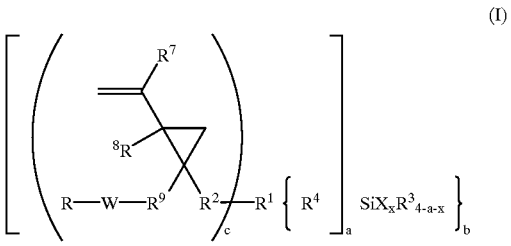

in which the variables R, $R^1$, $R^2$, $R^3$, $R^4$, $R^5$, $R^6$, $R^7$, $R^8$, $R^9$, W, X, Y, a, b, c, x, unless otherwise stated, independently of one another have the following meanings:

R=hydrogen, substituted or unsubstituted $C_1$ to $C_{12}$ alkyl, $C_7$ to $C_{15}$ alkylaryl or $C_6$ to $C_{14}$ aryl, or $R^3_{3-x}X_xSi$—$R_4$—$R_1$—$R_2$—;

$R^1$=missing or represents substituted or unsubstituted $C_1$ to $C_{18}$ alkylene, $C_6$ to $C_{18}$ arylene, $C_7$ to $C_{18}$ alkylenearylene or arylenealkylene, these radicals being able to be interrupted by at least one group selected from ether, thioether, ester, carbonyl, amide and urethane groups or being able to bear these in the terminal position;

$R^2$=missing or represents substituted or unsubstituted $C_1$ to $C_{18}$ alkylene, $C_6$ to $C_{18}$ arylene, $C_7$ to $C_{18}$ alkylenearylene or $C_7$ to $C_{18}$ arylenealkylene, these radicals being able to be interrupted by at least one group selected from ether, thioether, ester, thioester, carbonyl, amide and urethane groups or being able to bear these in the terminal position;

$R^3$=missing or represents substituted or unsubstituted $C_1$ to $C_{18}$ alkyl, $C_2$ to $C_{18}$ alkenyl, $C_6$ to $C_{18}$ aryl, $C_7$ to $C_{18}$ alkylaryl or $C_7$ to $C_{18}$ arylalkyl, these radicals being able to be interrupted by at least one group selected from ether, thioether, ester, carbonyl, amide and urethane groups;

$R^4$=missing or represents substituted or unsubstituted —$CHR^6$—$CHR^6$—, —$CHR^6$—$CHR^6$—S—$R^5$, —S—$R^5$—, —Y—CO—NH—$R^5$— or —CO—O—$R^5$—;

$R^5$=substituted or unsubstituted $C_1$ to $C_{18}$ alkylene, $C_6$ to $C_{18}$ arylene, $C_6$ to $C_{18}$ alkylenearylene or $C_6$ to $C_{18}$ arylenealkylene, these radicals being able to be interrupted by at least one group selected from ether, thioether, ester, carbonyl, amide and urethane groups;

$R^6$=hydrogen or substituted or unsubstituted $C_1$ to $C_{18}$ alkyl or $C_6$ to $C_{10}$ aryl;

$R^7$=hydrogen or substituted or unsubstituted $C_1$ to $C_{10}$ alkyl, or halogen or hydroxy;

$R^8$=hydrogen or substituted or unsubstituted $C_1$ to $C_{10}$ alkyl;

$R^9$ missing or represents substituted or unsubstituted $C_1$ to $C_{10}$ alkylene;

W=missing or represents carbonyl, ester, ether, thioether, amide or urethane groups;

X=a hydrolysable group, namely halogen, hydroxy, alkoxy or acyloxy;

Y=O or S;

a=1, 2 or 3;

b=1, 2 or 3;

c=1 to 6; and x=1, 2 or 3;

and with the proviso that (i) a+x=2, 3 or 4 and (ii) a and/or b=1.

However, the above formula covers only those compounds which are compatible with the valency theory.

The silanes according to the invention are usually present as stereoisomer mixtures and in particular as racemates.

The ether, thioether, ester, thioester, carbonyl, amide and urethane groups which are possibly present in the radicals are defined by the following formulae: —O—, —S—, —CO—O—, —O—CO—, —CO—S—, —S—CO—, —CS—O—, —O—CS—, —CO—, —CO—NH—, —NH—CO—, —O—CO—NH— and —NH—CO—O—.

The non-aromatic radicals or non-aromatic parts of the radicals possible in formula (I) can be straight-chained, branched or cyclic.

Alkyl radicals have preferably 1 to 8 and particularly preferably 1 to 4 carbon atoms. Particular examples of possible alkyl radicals are methyl, ethyl, n- and iso-propyl, sec- and tert-butyl, n-pentyl, cyclohexyl, 2-ethylhexyl and octadecyl.

Alkenyl radicals have preferably 2 to 10 and particularly preferably 2 to 6 carbon atoms. Particular examples of possible alkenyl radicals are vinyl, allyl and iso-butenyl.

Preferred examples of possible aryl radicals are phenyl, biphenyl and naphthyl.

Alkoxy radicals preferably have 1 to 6 carbon atoms. Particular examples of possible alkoxy radicals are methoxy, ethoxy, n-propoxy, iso-propoxy and tert-butoxy.

Acyloxy radicals preferably have 2 to 5 carbon atoms. Particular examples are acetyloxy and propionyloxy.

Preferred alkylene radicals are derived from the above preferred alkyl radicals and preferred arylene radicals are derived from the above preferred aryl radicals. Preferred radicals consisting of a combination of non-aromatic and aromatic parts, such as alkylaryl, arylalkyl, alkylenearylene and arylenealkylene radicals, are derived from the above preferred alkyl and aryl radicals. Particular examples thereof are benzyl, 2-phenylethyl and tolyl.

The stated substituted R radicals bear one or more simple substituents. Examples of these substituents are methyl, ethyl, phenyl, benzyl, hydroxymethyl, hydroxyethyl, methoxy, ethoxy, chloro, bromo, hydroxy, mercapto, isocyanato, vinyloxy, acryloxy, methacryloxy, allyl, styryl, epoxy, carboxy, $SO_3H$, $PO_3H_2$ or $PO_4H_2$.

For a, b, c or x$\geq$2, the radicals X and W and the individual R radicals can in each case have the same or a different meaning.

Moreover, preferred definitions exist for the above-stated variables of formula (I) which, unless otherwise stated, can be chosen independently of one another and are as follows:

R=$C_1$ to $C_5$ alkyl, benzyl or phenyl or $R^3_{3-x}X_xSi$—$R_4$—$R_1$—$R_2$—;

$R^1$=$C_1$ to C8 alkylene, these radicals being able to be interrupted by at least one group selected from ether, thioether, ester and urethane groups;

$R^2$=missing or represents $C_1$ to $C_8$ alkylene, these radicals being able to be interrupted by at least one group selected from ether, thioether, ester, thioester, carbonyl, amide and urethane groups or being able to bear these in the terminal position;

$R^3$=missing or represents methyl, ethyl or phenyl;

$R^4$=missing or represents —$CHR^6$—$CHR^6$—, —S—$R^5$—, —Y—CO—NH—$R^5$— or —CO—O—$R^5$—, $R^5$=$C_1$ to $C_8$ alkylene, these radicals being able to be interrupted by at least one group selected from ether, thioether, ester, carbonyl, amide and urethane groups;

$R^6$=hydrogen or $C_1$ to $C_5$ alkyl;

$R^7$=hydrogen or $C_1$ to $C_5$ alkyl;

$R^8$=hydrogen or $C_1$ to $C_5$ alkyl;

$R^9$=missing or represents $C_1$ to $C_3$ alkylene;

W=ester, amide or urethane group;

X=methoxy, ethoxy or chloro;

Y=O or S;

a=1;

b=1;

c=1 to 6;

x=2 or 3; and/or a+x=3.

The individual R radicals can in turn bear simple substituents.

Preferred compounds are accordingly those in which at least one of the variables of formula (I) has the above-described preferred definition.

Furthermore, those vinylcyclopropane silanes of formula (I) are preferred in which the indices a, b and/or c have the value 1 and examples thereof are the silanes according to the general formulae (II), (III), (IV) and (V) below.

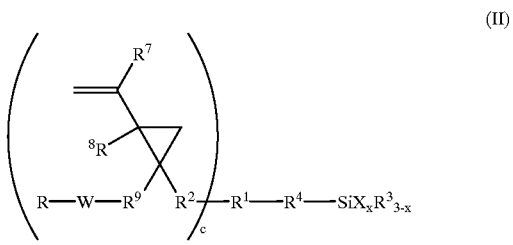

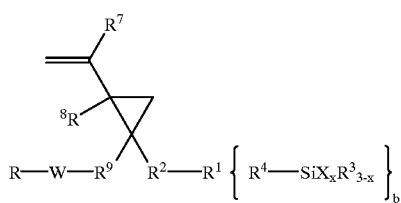
(III)
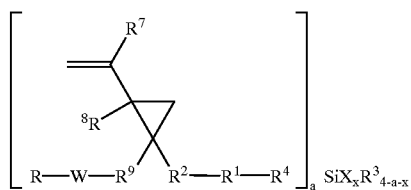
(IV)
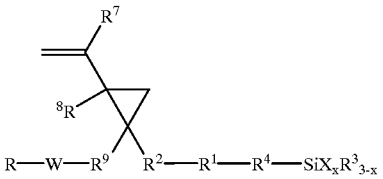
(V)
Particular examples of preferred vinylcyclopropane silanes according to the invention of formula (I) are given below:
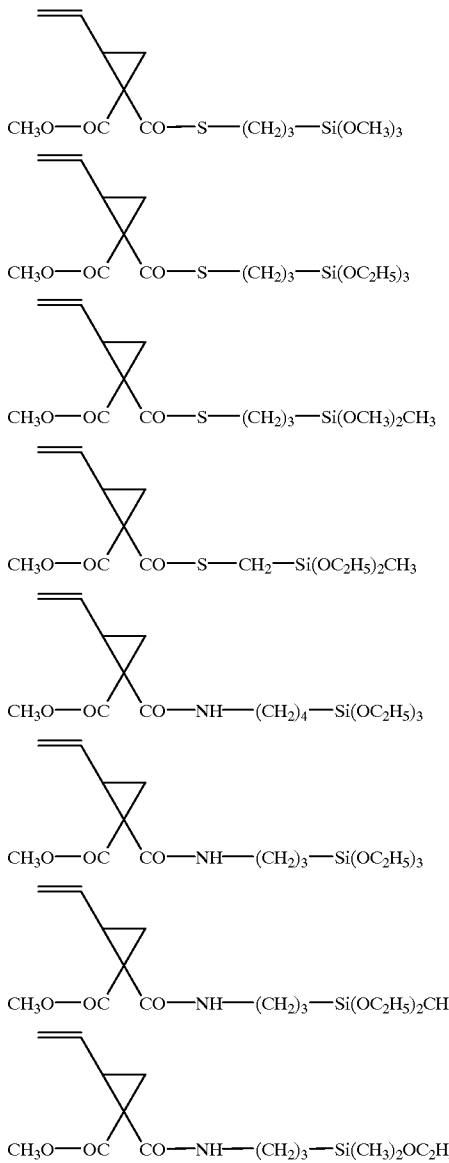

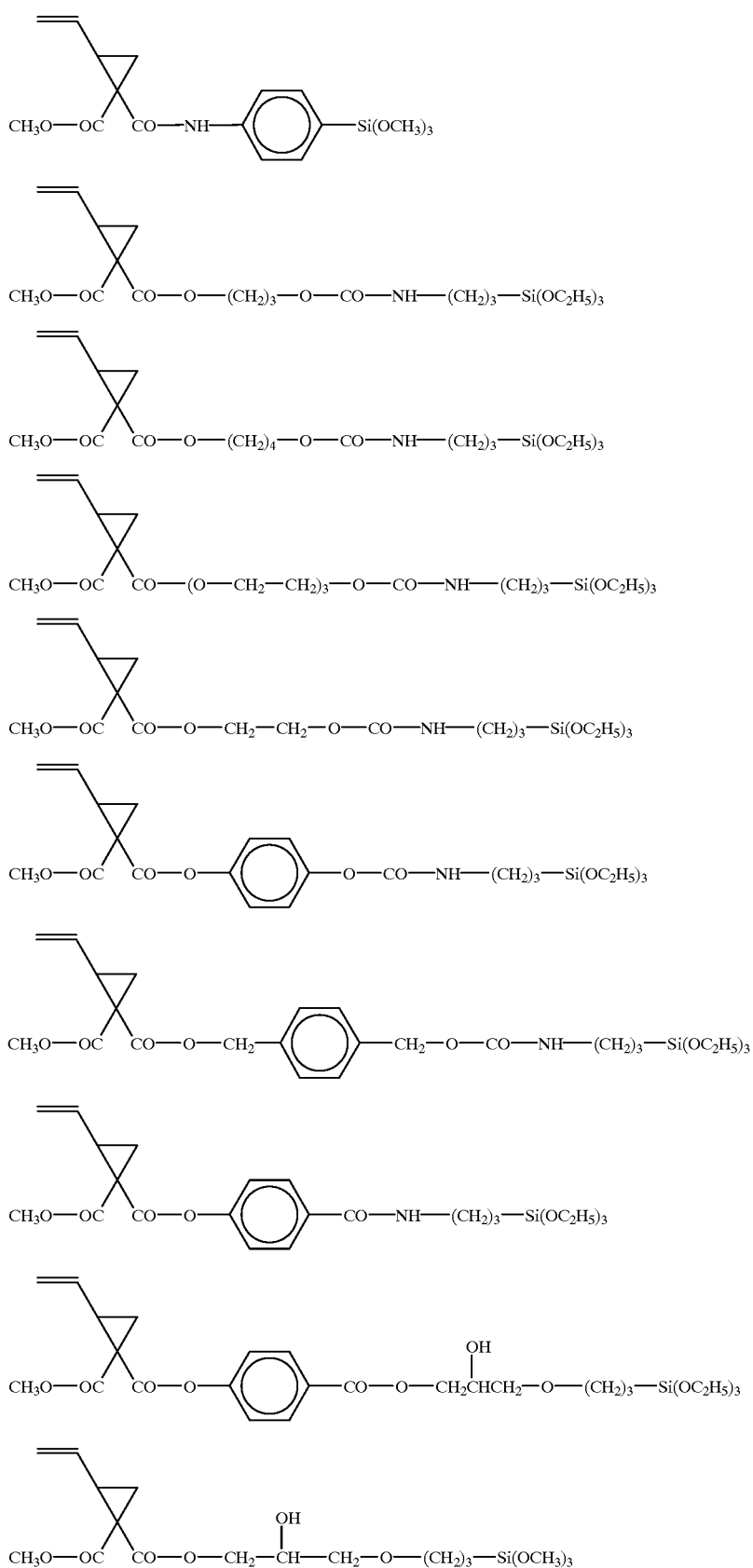

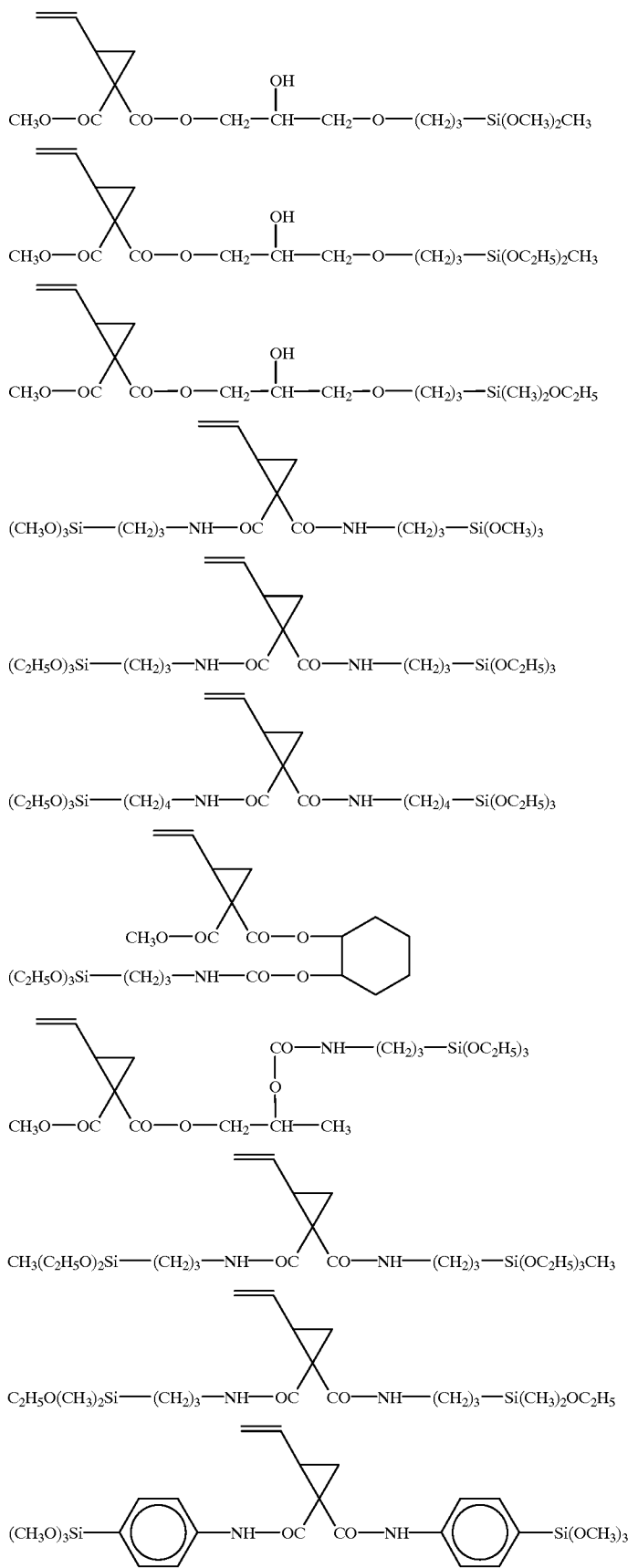

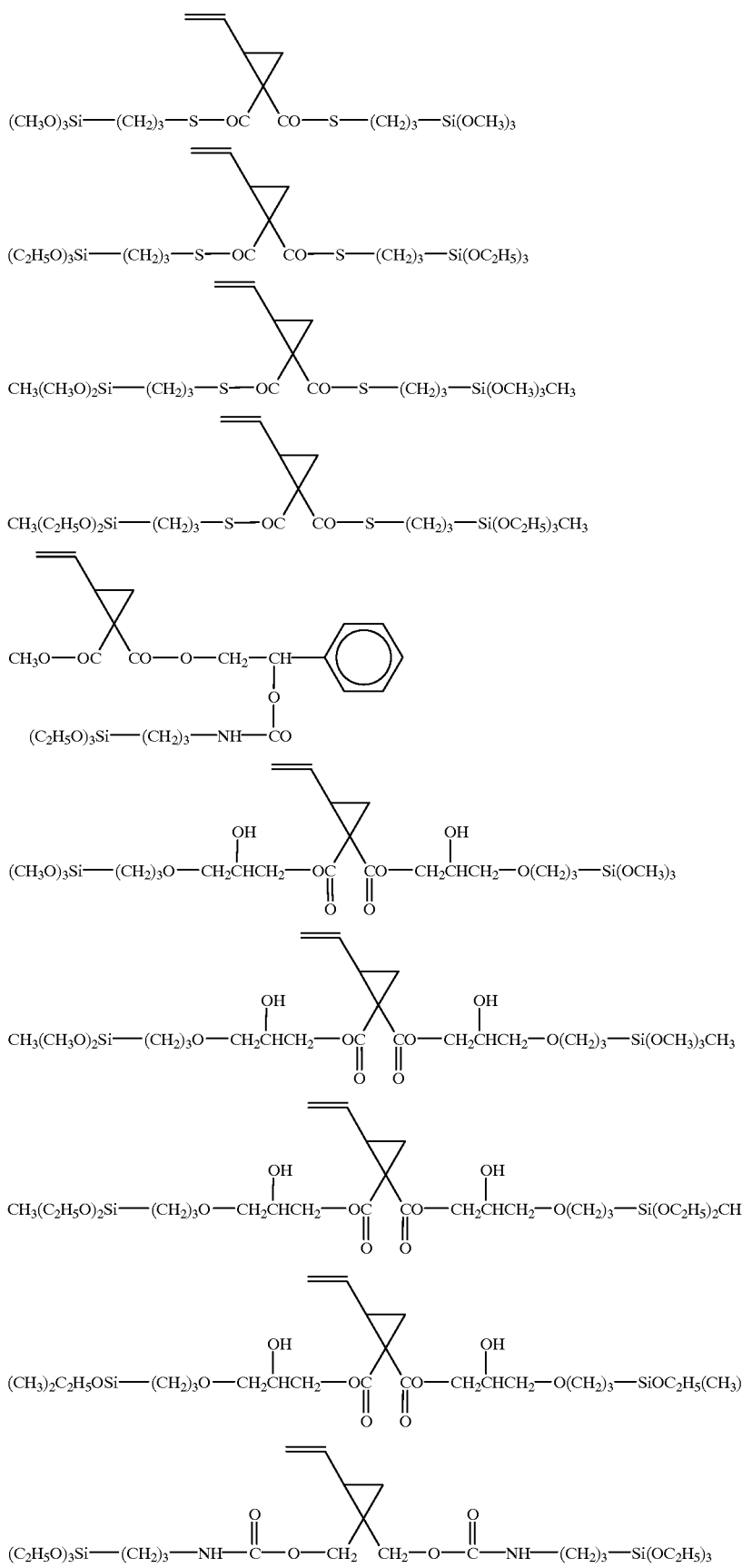

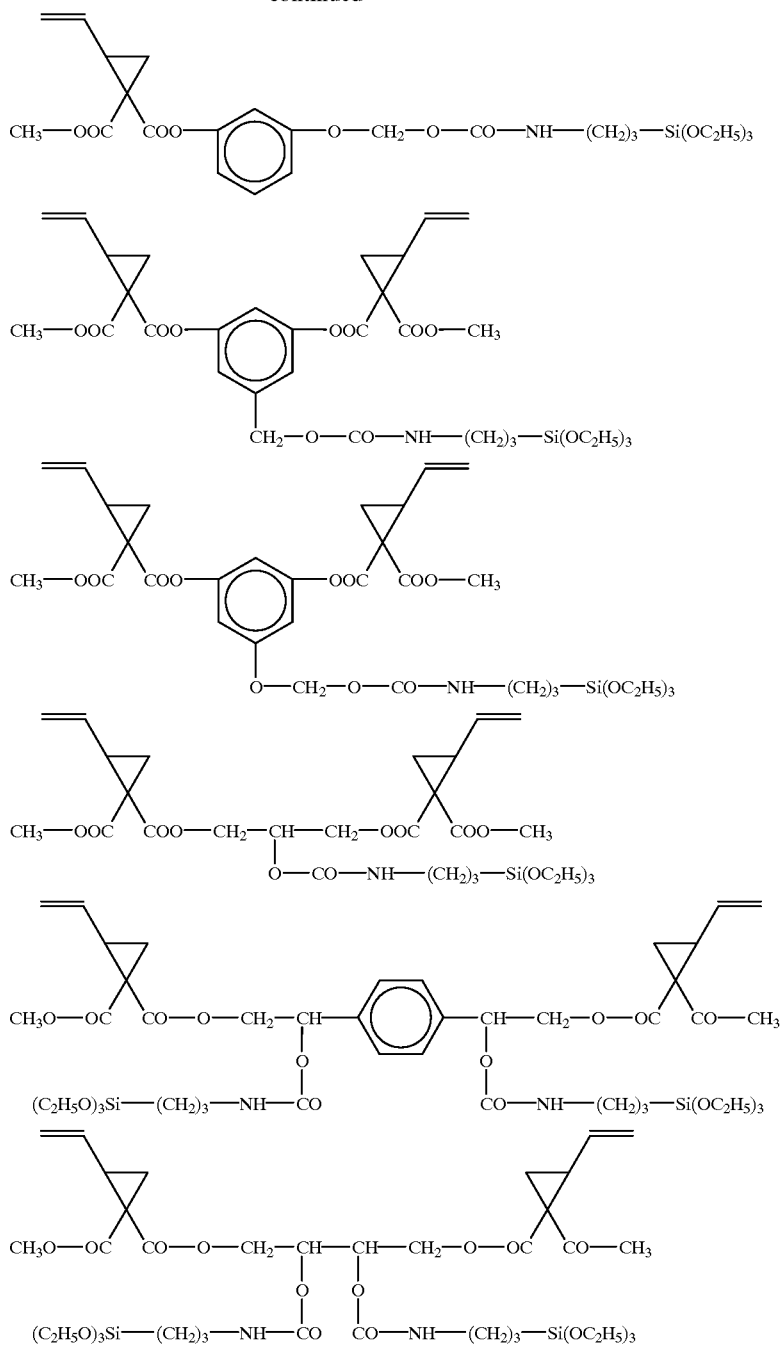

The preparation of the vinylcyclopropane silanes (I) according to the invention is possible in particular via a large numnber of conventional addition or condensation reactions which are carried out according to the methods customary for these reactions. Processes which can be used for preparing the silanes according to the invention are described e.g. in W. Noll, Chemie und Technologie der Silicone, 2nd edition, Verlag Chemie, Weinheim, 1968, in particular p. 22 et seq., and in the review by R. C. Mehrotra in J. Non-Crystalline Solids 100, (1988) 1–15 and the literature quoted in this article.

In a first variant, e.g. 1-methoxycarbonyl-2-vinylcyclopropane-1-carboxylic acid (1) or the acid chloride or potassium salt thereof can be reacted with amino- or mercapto-functionalized silanes by means of a nucleophilic substitution.

Nucleophilic substitution:

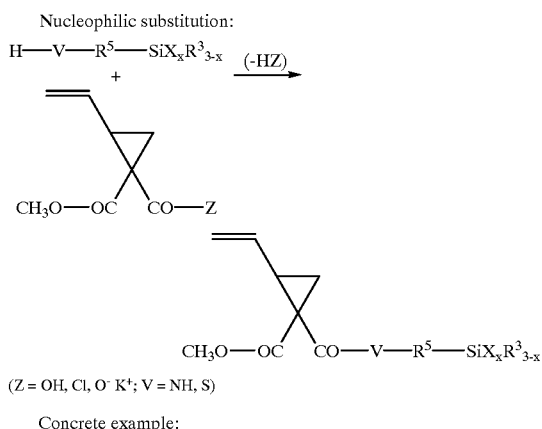

($Z = OH, Cl, O^- K^+$; $V = NH, S$)

Concrete example:

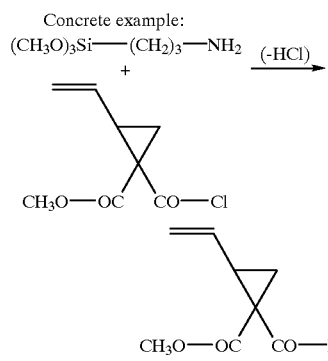

Analogously thereto, the acid (1) can also be added to an isocyanate group-containing silane:

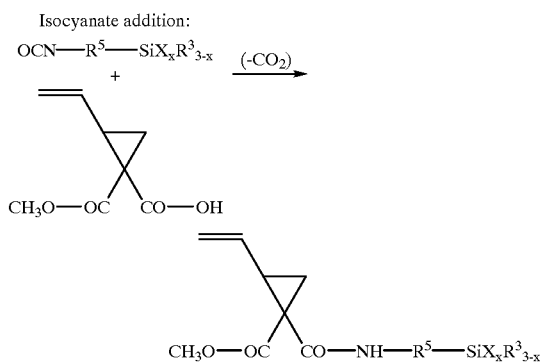

Concrete example:

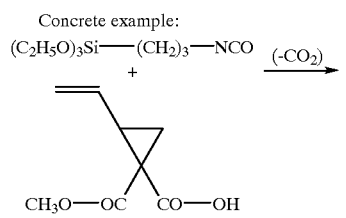

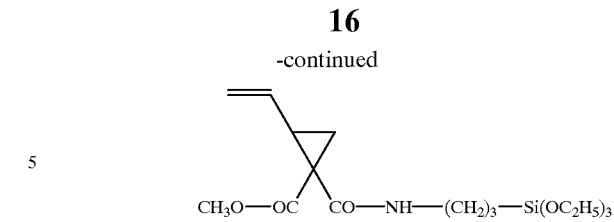

Furthermore, the addition of the acid (1) to an epoxide silane is possible:

Epoxide addition:

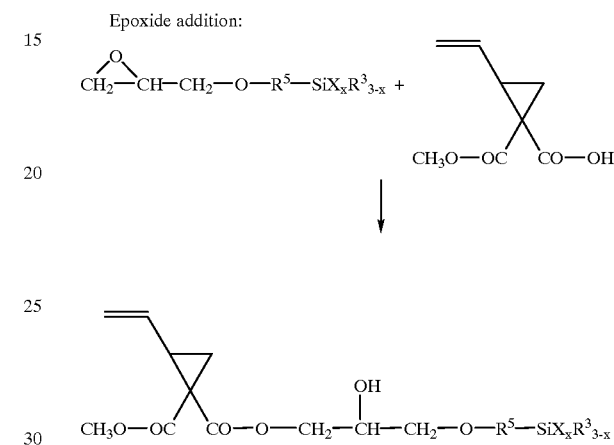

Concrete example:

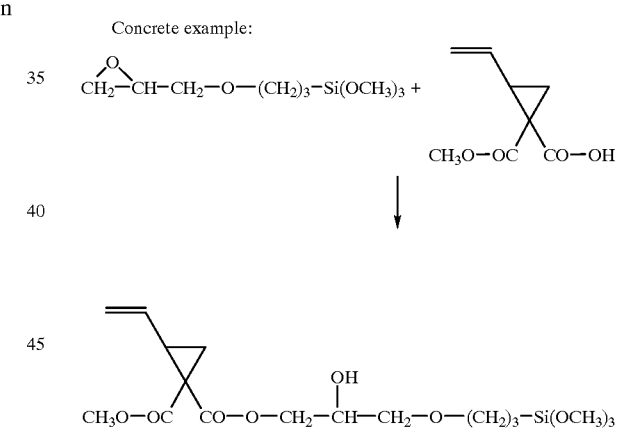

Silanes with $R=R^3_{3-x}X_xSi-R_4-R_1-R_2-$ can also be prepared in a corresponding manner, in place of the acid (1) the 2-vinylcyclopropane-1,1-dicarboxylic acid (2) or the acid chloride or potassium salt thereof being reacted with e.g. amino- or mercapto-functionalized silanes by means of a nucleophilic substitution.

Nucleophilic substitution:
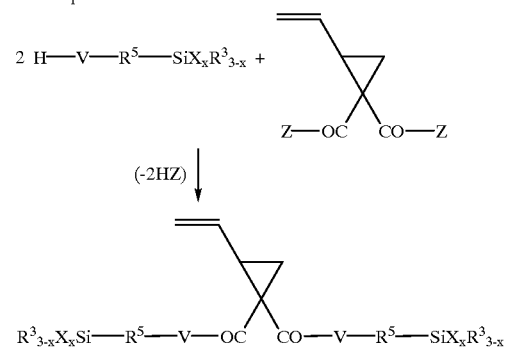
(Z = OH, Cl, O⁻ K⁺; V = NH, S)
Concrete example:
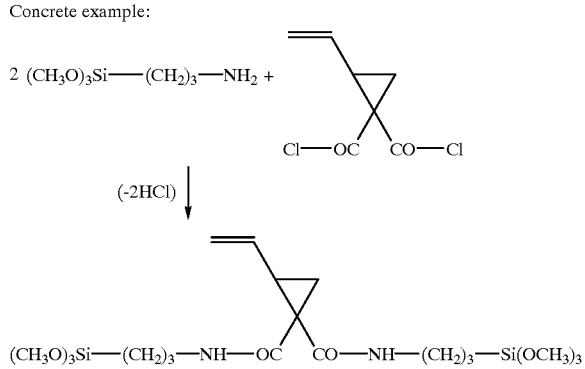
Epoxide addition:
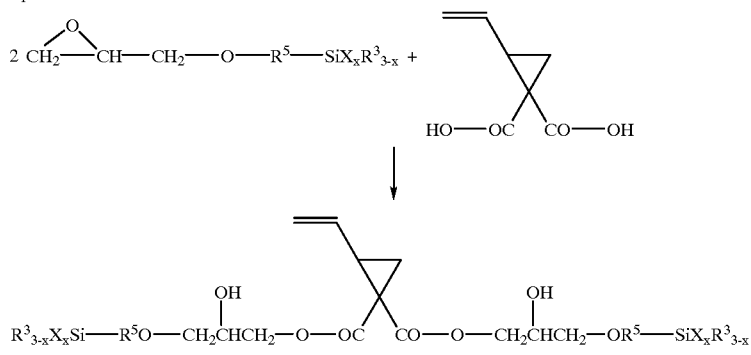
Concrete example:
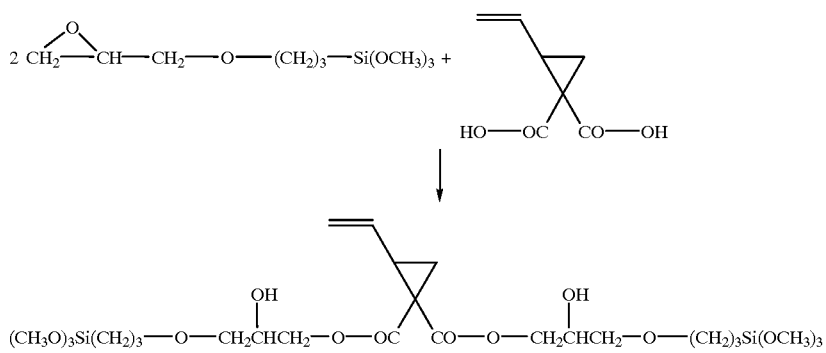
Finally, 1,1-bis (hydroxymethyl) -2-vinylcyclopropane (3) can also be added to isocyanate-containing silanes:

Isocyanate addition:

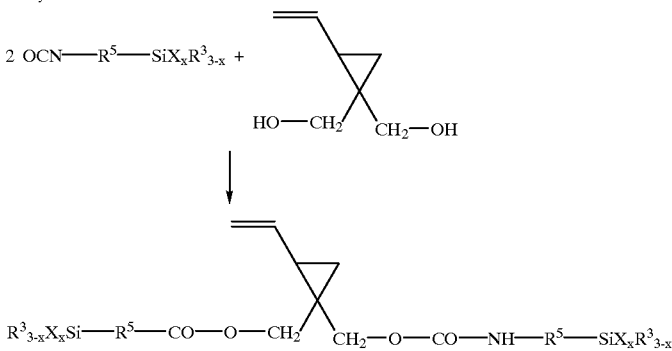

Concrete example:

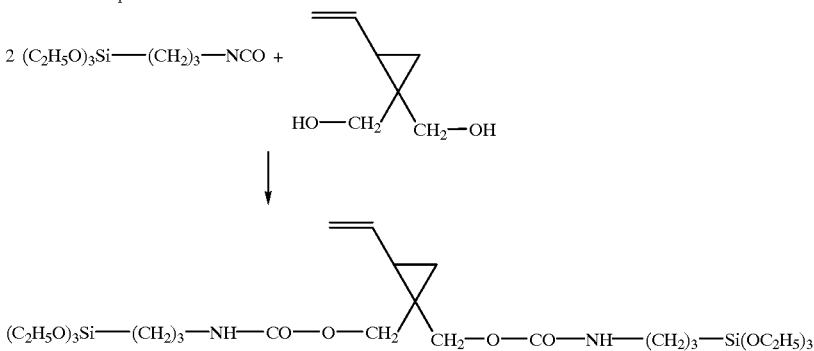

The individual synthesis methods can also be combined. For example, multifunctional silanes can be obtained by combining the epoxide addition with the isocyanate addition, such as

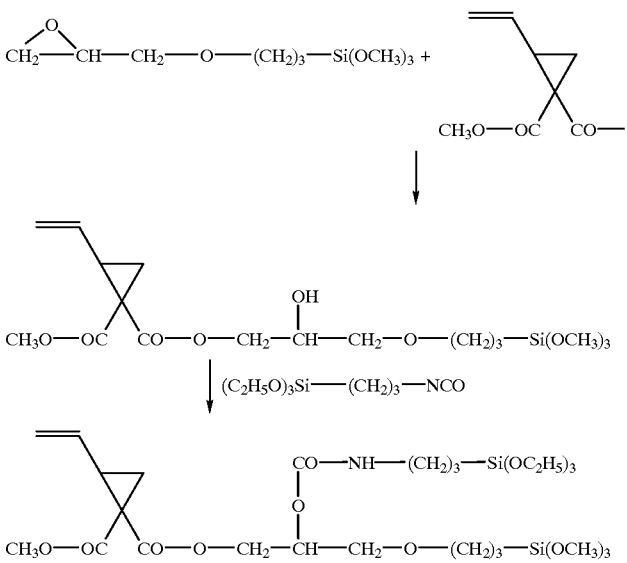

The silanes (I) according to the invention are polymerizable via the C=C double bonds of the 2-vinylcyclopropane radicals and hydrolysable via the radicals X. The polymerization of the 2-vinylcyclopropane groups leads to the formation of an organic network, whereas the hydrolysable groups produce an inorganic polysiloxane network through polycondensation.

The vinylcyclopropane silanes according to the invention are substances of high reactivity which on hydrolysis form polymerizable silicic acid condensates which can be polymerized in the presence of radical initiators thermally or by irradiation with light of the visible or UV range to form mechanically stable layers, moulded articles or fillers.

The number of hydrolysable groups, polymerizable groups and further functional groups can be varied by suitable selection of the starting materials used in the preparation of the vinylcyclopropane silanes. Depending on the type and number of the hydrolysable groups and on the number of vinylcyclopropane groups, the condensation of the vinylcyclopropane silanes and the polymerization of the obtained condensates results in materials with properties which range from silicone rubber-like to glass-like.

The development of a three-dimensional, organic network is possible when at least two vinylcyclopropane radicals are present, the mechanical properties, such as e.g. strength and flexibility, and the physico-chemical properties, e.g. adhesiveness, water absorption and refractive index, of the obtained silicic acid condensates being variable and optimally adaptable to the requirements of the respective case of application via the distance between the Si atom and the vinylcyclopropane radical, i.e. via the length of the spacer group, and by incorporation of further functional groups. Aliphatic groups result in products which are rather flexible, and aromatic groups result in products which are rather rigid.

Furthermore, the crosslinking density, which then likewise influences the properties and possible applications of the corresponding silicic acid condensates formed, can be set by means of the number of polymerizable vinylcyclopropane groups. Moreover, if the vinylcyclopropane silanes according to the invention also contain ionically crosslinkable groups as substituents, such as epoxy groups, then a further increase in crosslinking density can be achieved simultaneously or consecutively, i.e. as a 2-stage process, by their ionic polymerization.

The vinylcyclopropane silanes according to the invention and their silicic acid condensates possess only a low volatility, with the result that they can be processed in an easy and largely harmless manner. In view of the above-stated variation possibilities of the condensable and polymerizable radicals of the vinylcyclopropane silanes according to the invention, silicic acid condensates which can be prepared therefrom can be provided as resins or fillers for very different areas of application.

The silanes (I) are stable compounds which can be processed either alone or together with other hydrolysable, condensable and/or polymerizable components to form the silicic acid condensates according to the invention.

In addition to the silanes of formula (I), other hydrolytically condensable compounds of silicon, aluminium, titanium, zirconium or phosphorus can be used in the preparation of the silicic acid condensates according to the invention, which are then also referred to as silicic acid (hetero)condensates. These compounds can be used either as such or in already precondensed form. It is preferred that at least 20 mol. %, particularly preferably at least 80 mol. %, based on monomeric compounds, of hydrolysable silicon compounds are used for the preparation of the silicic acid (hetero)condensates according to the invention. It is also preferred that at least 10 mol. %, in particular 40 to 100 mol. %, in each case based on monomeric compounds, of vinylcyclopropane silanes according to the invention are used for the preparation of the silicic acid (hetero)condensates.

Preferably at least one silane of the general formula (VI) is used as other hydrolytically condensable compounds:

$$R^{10}{}_k(Z'R^{11})_m SiX'_{4-(k+m)} \quad (VI)$$

in which $R^{10}$, $Z'$, $R^{11}$, $X'$, k and m, unless otherwise stated, independently of one another have the following meanings:

$R^{10}$=$C_1$ to $C_8$ alkyl, $C_2$ to $C_{12}$ alkenyl or $C_6$ to $C_{14}$ aryl;
$R^{11}$=$C_1$ to $C_8$ alkylene, $C_2$ to $C_{12}$ alkenylene or $C_6$ to $C_{14}$ arylene;
X'=hydrogen, halogen or $C_1$ to $C_8$ alkoxy;
Z'=mercapto, glycidyl, acrylic, methacrylic, vinyl, allyl or vinyl ether group;
k=0, 1, 2 or 3;
m=0, 1, 2 or 3; and
k+m=1, 2 or 3.

Such silanes are described e.g. in DE-C-34 07 087, and particular examples of hydrolytically condensable silanes of general formula (VI) are:
$CH_3$—Si—$Cl_3$, $CH_3$—Si—$(OC_2H_5)_3$, $C_2H_5$—Si—$Cl_3$, $C_2H_5$—Si—$(OC_2H_5)_3$, $CH_2$=CH—Si—$(OC_2H_5)_3$, $CH_2$=CH—Si—$(OCH_3)_3$, $CH_2$=CH—Si—$(OC_2H_4OCH_3)_3$, $(CH_3)_2$—Si—$Cl_2$, $(CH_3)_2$—Si—$(OC_2H_5)_2$, $(C_2H_5)_3$—Si—Cl, $(C_2H_5)_2$—Si—$(OC_2H_5)_2$, $(CH_3)_3$—Si—Cl, $(CH_3O)_3$—Si—$C_3H_6$—$NH_2$, $(CH_3O)_3$—Si—$C_3H_6$—SH, $(CH_3O)_3$—Si—$C_3H_6$—$NH_2$,

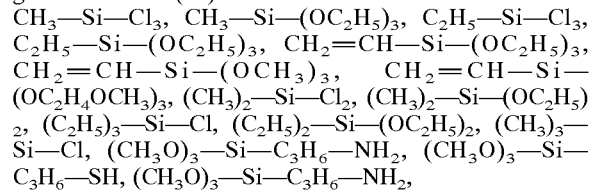

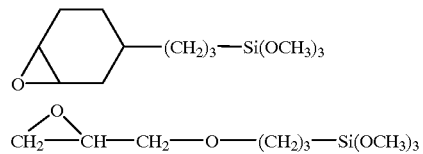

Furthermore, at least one zirconium, titanium or aluminium compound of the formulae $$MeX''R^{12}{}_z AlR^{13}{}_3$$

can be used as other preferred hydrolytically condensable compounds, in which Me, $R^{12}$, $R^{13}$, X", y and z independently of one another have the following meanings:

Me=Zr or Ti;
$R^{12}$=hydrogen, substituted or unsubstituted $C_1$ to $C_{12}$ alkyl, $C_7$ to $C_{15}$ alkylaryl or $C_6$ to $C_{14}$ aryl;
$R^{13}$=halogen, OH, $C_1$ to $C_8$ alkoxy;
X"=halogen, OH, $C_1$ to $C_8$ alkoxy;
y=1 to 4, in particular 2 to 4;
z=1 to 3, in particular 0 to 2.

Preferred examples of zirconium and titanium compounds which can be used are $ZrCl_4$, $Zr(OC_2H_5)_4$, $Zr(OC_3H_7)_4$, $Zr(OC_4H_9)_4$, $ZrOCl_2$, $TiCl_4$, $Ti(OC_2H_5)_4$, $Ti(OC_3H_7)_4$ and $Ti(OC_4H_9)_4$. Preferred examples of aluminium compounds which can be used are $Al(OCH_3)_3$, $Al(OC_2H_5)_3$, $Al(OC_3H_7)_3$, $Al(OC_4H_9)_3$ and $AlCl_3$.

Complexed Zr, Ti and Al compounds can also be used, in which inter alia acids or β-dicarbonyl compounds can act as complexing agents.

Other hydrolysable compounds which can be used for preparing the silicic acid (hetero)condensates are e.g. boron trihalides, tin tetrahalides, tin tetraalkoxides and vanadyl compounds.

The silicic acid condensates according to the invention of the silanes (I) are obtained by hydrolysis of the hydrolysable groups X present, e.g. alkoxy groups, and by subsequent condensation, which results in the formation of an inorganic network of Si—O—Si units. The hydrolysis and condensation usually take place in basic or acidic medium, a linking of C=C double bonds which are contained in the silanes used being generally undesired.

The silicic acid condensates according to the invention can also be present in incompletely hydrolysed and condensed form. In such cases, they are referred to as so-called precondensates.

The customary procedure in the preparation of the silicic acid (hetero)condensates according to the invention is that the silanes (I), optionally dissolved in a solvent, are reacted at room temperature or with slight cooling and in the presence of a hydrolysis and condensation catalyst with the necessary quantity of water, and the resulting mixture is stirred for one to several hours. Coming into consideration as solvents are above all aliphatic alcohols, such as ethanol or i-propanol, dialkyl ketones, such as acetone or methyl isobutyl ketone, ethers, such as diethyl ether or tetrahydrofuran (THF), esters, such as ethyl or butyl acetate, and mixtures thereof.

If the hydrolytic condensation is carried out in the presence of reactive Zr, Ti or Al compounds, the addition of water should take place in stages at ca. 0 to 30° C. It is usually favourable not to add water as such, but to introduce it in the form of water-containing solvents, such as aqueous ethanol, or by release via a chemical reaction, such as via an esterification.

The hydrolysis and condensation preferably takes place in the presence of a condensation catalyst, preference being given to proton- or hydroxyl ion-releasing compounds, such as organic or inorganic acids or bases. Particularly preferred are volatile acids or bases, in particular hydrochloric acid or ammonia. It has proved to be worthwhile for the hydrolysis and condensation to adopt procedures of sol-gel technology, as are described e.g. in C. J. Brinker et al., "Sol-Gel Science", Academic Press, Boston, 1990. The "sol-gel process" is also disclosed in DE-A-27 58 414, DE-A-27 58 415, DE-A-30 11 761, DE-A-38 26 715 and DE-A-38 35 968.

The obtained silicic acid (hetero)condensates of the silanes (I) and optionally of other hydrolytically condensable compounds can be used either as such or after partial or complete removal of the solvent used. In some cases, it can also prove to be advantageous to replace the solvent used for the hydrolytic condensation with another solvent.

The polymerizable silicic acid (hetero)condensates according to the invention and the silanes (I) and compositions containing these condensates or silanes can be cured by thermal, photochemical or redox-induced polymerization, the polymerization usually taking place after suitable initiators and other polymerizable components have been added. If different polymerizable groups, e.g. vinylcyclopropane and epoxide groups, are present, several curing mechanisms, e.g. radical and cationic polymerization, can also be used simultaneously or in successive stages.

Thermal initiators and/or photoinitiators are preferably used to initiate the radical polymerization. Preferred examples of thermal initiators are the known peroxides, such as dibenzoyl peroxide, dilauryl peroxide, tert-butyl peroctoate or tert-butyl perbenzoate, and also azobisisobutyroethyl ester, benzpinacol or 2,2-dimethylbenzpinacol.

Examples of suitable photoinitiators are benzophenone, benzoin and derivatives thereof or α-diketones or derivatives thereof, such as 9,10-phenanthrenequinone, diacetyl or 4,4-dichlorobenzil. Camphor quinone and 2,2-methoxy-2-phenyl-acetophenone are preferably used, and α-diketones in combination with amines as reducing agents, such as N-cyanoethyl-N-methylaniline, 4-(N,N-dimethylamino) benzoic acid ester, N,N-dimethylaminoethyl methacrylate, N,N-dimethyl-sym-xylidine or triethanolamine are particularly preferably used. Particularly suitable are also acyl phosphines, such as 2,4,6-trimethylbenzoyldiphenyl- or bis (2,6-dichlorobenzoyl)-4-N-propylphenylphosphine oxide.

Particularly suitable for the dual curing of radically and cationically polymerizable compounds are diaryliodonium or triarylsulphonium salts, such as triphenylsulphonium hexafluorophosphate or hexafluoroantimonate.

Redox-initiator combinations, such as combinations of benzoyl or lauryl peroxide with N,N-dimethyl-sym-xylidine or N,N-dimethyl-p-toluidine, are used as initiators for a polymerization carried out at room temperature.

In the compositions according to the invention, suitable polymerizable mono- or multifunctional monomers which can also be referred to as diluent monomers can also be present in addition to the silanes (I) or the corresponding silicic acid (hetero)condensates. Particularly preferred diluent monomers are above all mono- and multifunctional vinylcyclopropane derivatives, such as 1,1-bis (alkoxycarbonyl)- or 1,1-bis(aryloxycarbonyl)-2-vinylcyclopropanes, e.g. 1,1-bis-(methoxycarbonyl)-, 1,1-bis(ethoxycarbonyl)- or 1,1-bis-(phenoxycarbonyl)-2-vinylcyclopropane, or bis(2-vinylcyclopropane-1-alkoxycarbonyl-1-carbonyloxy) derivatives, e.g. bis(2-vinylcyclopropane-1-methoxycarbonyl-1-carbonyloxy) ethane or bis (2-vinylcyclopropane-1-methoxycarbonyl-1-carbonyloxy)benzene. Moreover, other radically polymerizable diluent monomers such as monofunctional (meth) acrylates, e.g. methyl (meth)acrylate, ethyl (meth)acrylate, butyl (meth)acrylate, benzyl (meth)acrylate, furfuryl (meth) acrylate or phenyl (meth)acrylate, and polyfunctional (meth) acrylates, e.g. bisphenyl-A-di(meth)acrylate, bis-GMA (an addition product of methacrylic acid and bisphenol-A-diglycidyl ether), UDMA (an addition product of 2-hydroxyethyl methacrylate and 2,2,4-hexamethylene diisocyanate), di-, tri- or tetraethylene glycol di(meth) acrylate, decanediol di(meth)acrylate, trimethylolpropane tri(meth)acrylate, pentaerythritol tetra(meth)acrylate, butanediol di(meth)acrylate, 1,10-decanediol di(meth) acrylate or 1,12-dodecanediol di(meth)acrylate, can also be used.

The silanes according to the invention, the silicic acid condensates or silicic acid heterocondensates thereof and compositions containing them can be used as such or in at least partially polymerized form e.g. as varnishes for coating plastics, glass or other substrates, as fillers or bulk material for composites and in particular for medical materials, e.g. for the production of contact lenses. They are, however, particularly preferably used as dental material or a constituent thereof.

The compositions according to the invention can also optionally contain other additives, such as coloring agents (pigments or dyes), stabilizers, flavorants, microbiocidal active ingredients, flameproofing agents, plasticizers or UV absorbers.

Other possible additives are fillers. Examples of preferred fillers are quartz, glass ceramic or glass powders, in particular barium or strontium silicate glass powder, lithium-aluminium silicate glass powder, silicon, zirconium or aluminium oxides, or mixtures thereof, finely divided silicas, in particular pyrogenic or precipitated silicas, and X-ray-opaque fillers, such as e.g. ytterbium trifluoride.

A particularly preferred composition according to the invention contains:

(a) 5 to 90, in particular 10 to 70 wt. %, relative to the composition, of silicic acid (hetero)condensate of a silane (I), (b) 0 to 80, in particular 0 to 50 wt. %, relative to the composition, of diluent monomer, (c) 0.1 to 5, in particular 0.2 to 2.0 wt. %, relative to the composition, of polymerization initiator, and/or (d) 0 to 90, in particular 0 to 80 wt. %, relative to the composition, of fillers.

The compositions according to the invention are particularly preferably used as dental cement, dental filling material or dental bonding for filling materials. The compositions are used in particular by applying them to the area of a false or natural tooth to be treated and curing by polymerization.

It proves to be a particular advantage of the compositions according to the invention that on the one hand they exhibit a low polymerization shrinkage and on the other hand they result in composite materials with high mechanical strength. Such a combination of properties is of particular significance especially in the case of dental materials.

The invention is explained below with reference to examples.

EXAMPLE 1

Synthesis of 1-methoxycarbonyl-1-[(3-triethoxysilyl)propylaminocarbonyl)]-2-vinylcyclopropane (4)

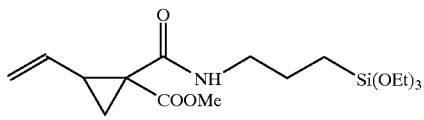

(4)

14.5 g (58.8 mmol) of isocyanatopropyltriethoxysilane were added dropwise to an ice-cooled solution of 10 g (58.8 mmol) of 2-vinylcyclopropane-1,1-dicarboxylic acid monomethyl ester and 20 mg of dibutyl tin dilaurate in 20 ml of methylene chloride. After 2 days stirring at room temperature, no more isocyanate was detectable using IR spectroscopy. After distilling off, 22 g of a faintly coloured liquid remained.

$^1$H-NMR (CDCl$_3$): 0.6 (t, 2H, CH$_2$Si), 1.25 (m, 11H, CH$_2$, CH$_3$), 1.62 (m, 2H, CH$_2$), 2.6 (m, 1H, CH), 3.16 (t, 2H, CH$_2$), 3.8 (q, 9H, OCH$_2$, OCH$_3$), 4.80–5.00 (br, 1H, NH), 5.1–5.8 (m, 3H, CH=CH$_2$) ppm.

IR (Film): 3355, 2979, 1718, 1081 cm$^{-1}$.

EXAMPLE 2

Synthesis of 1,1[bis-(triethoxysilylpropylaminocarboxymethyl)]-2-vinylcyclopropane (5)

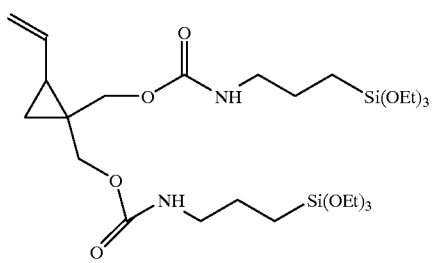

(5)

8 g (32 mmol) of 3-isocyanatopropyltriethoxysilane were added carefully to a solution of 2 g (16 mmol) of bis(hydroxymethyl)-2-vinylcyclopropane and 20 mg of dibutyl tin dilaurate in 50 ml of dry methylene chloride. After 48 hours stirring under reflux, no more isocyanate was detectable using IR spectroscopy. After the solvent had been distilled off, 10 g (100% yield) of a clear liquid remained.

$^1$H-NMR (CDCl$_3$): 5.00–5.65 (m, 3H, CH=CH$_2$), 4.99 (br, 2H, NH), 3.99 (m, 4H, CH$_2$O), 3.83 (q, 12H, CH$_2$O), 3.18 (t, 4H, CH$_2$N), 1.76 (m, 3H, CH-cyclopropyl), 1.22 (m, 22H, CH$_2$, CH$_3$), 0.61 (t, 4H, CH$_2$Si) ppm.

IR (Film): 3444, 2976, 1718, 1517, 1266, 1077 cm$^{-1}$.

EXAMPLE 3

Synthesis of the adduct (6) of isocyanatopropyltriethoxysilane to 1-methoxycarbonyl-2-vinylcyclopropane-1-carboxylic acid-(2-hydroxy-3-phenoxy)prop-1-yl ester

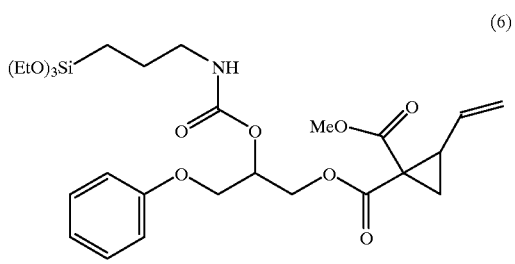

(6)

6.1 g (19 mmol) of 1-methoxycarbonyl-2-vinylcyclopropane-1-carboxylic acid-(2-hydroxy-3-phenoxy)prop-1-yl ester, which was obtained by adding 1-methoxycarbonyl-2-vinylcyclopropane-1-carboxylic acid to phenylglycidyl ether, 4.7 g (19 mmol) of isocyanatopropyltriethoxysilane and 20 mg of dibutyl tin dilaurate were stirred under argon and under reflux for 4 days until no more isocyanate was detectable using IR spectroscopy. After the solvent had been distilled off, 10.5 g (97% yield) of a yellow viscous liquid remained.

$^1$H-NMR (CDCl$_3$): 0.5–0.6 (t, 2H, CH$_2$Si), 1.2 (m, 11H, CH$_2$, CH$_3$), 1.5–1.8 (m, 2H, CH$_2$), 2.6 (m, 1H, CH), 3.1–3.4 (t, 2H, CH$_2$), 3.6–3.9 (m, 11H, OCH$_2$, OCH$_3$), 4.1 (m, 1H, CHO), 5.1–5.4 (br, 1H, NH), 6.8–7.3 (5 H$_{arom.}$) ppm.

IR (Film): 3385, 2974, 2928, 1729, 1600 cm$^{-1}$.

EXAMPLE 4

Di-adduct (7) of 3-isocyanatopropyltriethoxysilane to bis [(((1,4-(2-vinyl-1-methoxycarbonyl)-cyclopropan-1-yl)-carbonyloxy)-2-hydroxypropoxy)-methyl]-cyclohexane

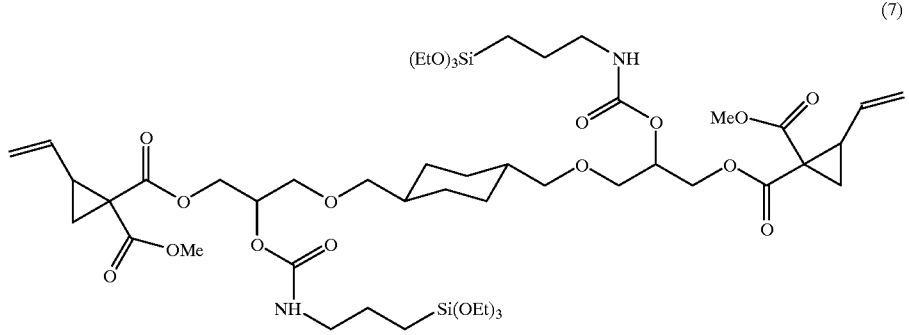

(7)

8 g (13.4 mmol) of bis[(((1,4-(2-vinyl-1-methoxycarbonyl)-cyclopropan-1-yl)-carbonyloxy)-2-hydroxypropoxy)-methyl]-cyclohexane (di-adduct of 1-methoxycarbonyl-2-vinylcyclopropane-1-carboxylic acid to 1,4-cyclohexanedimethanoldiglycidyl ether) and 6.6 g (26.8 mmol) of 3-isocyanatopropyltriethoxysilane and 20 mg of dibutyl tin dilaurate were heated under reflux for 4 days in 20 ml of dry methylene chloride, until no more isocyanate was detectable using IR spectroscopy. After the solvent had been distilled off, 13.2 g (90% yield) of a yellow, viscous liquid remained.

$^1$H-NMR (CDCl$_3$): 0.55–0.66 (t, 4H, CH$_2$Si), 1.15–1.25 (m, 22H, CH$_3$, —CH$_2$—CH$_2$—CH$_2$—), 1.3–1.8 (br. m, 14H, cyclohexyl, cyclopropyl-CH$_2$), 2.55–2.65 (m, 2H, CH), 3.1–3.3 (m, 4H, CH$_2$N), 3.4–3.7 (m, 12H, CH$_2$O), 3.75 (s, 6H, OCH$_3$), 3.85 (t, 4H, CH$_2$), 4.1–4.4 (m, 2H, CHO), 5.01 (br, 2H, NH), 5.25–5.55 (m, 6H, CH=CH$_2$), ppm.

IR (Film): 3354, 2975, 1728, 1527, 1078 cm$^{-1}$.

EXAMPLE 5

Hydrolytic condensation of 1-methoxycarbonyl-1-[(3-triethoxysilyl)propylaminocarbonyl)]-2-vinylcyclopropane (4)

100 mmol of the silane (4) were dissolved in 15 ml of anhydrous ethanol or THF. Hydrolysis took place by adding 150 mmol of water in the form of 0.1 N aqueous HCl. After 72 hours stirring at room temperature, the volatile components were removed in vacuo and there formed a viscous resin which could be used as monomer component for a radical polymerization, e.g. as component for a radically curable dental material.

EXAMPLE 6

Hydrolytic condensation of 1.1-[bis-(triethoxysilylpropylaminocarboxymethyl)]-2-vinylcyclopropane (5)

100 mmol of the silane (5) were dissolved in 25 ml of anhydrous ethanol or THF. Hydrolysis took place by adding 150 mmol of water in the form of 0.1 N aqueous HCl. After 2 to 4 hrs stirring at room temperature, the volatile components were removed in vacuo and there formed a viscous resin which, after radical initiator had been added, could be used as component for a light-curing coating or a light-curing dental material.

EXAMPLE 7

Product of addition of 3-aminopropyltriethoxysilane to 1-(2-acrylocyloxyethyloxycarbonyl)-1-methoxycarbonyl-2-vinylcyclopropane

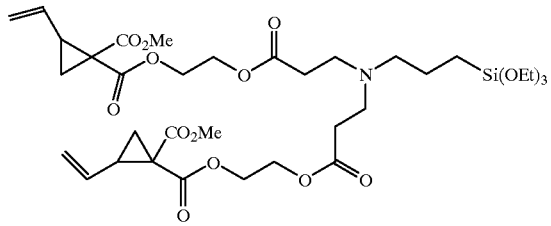

A mixture of 6.2 g (28 mmol) 3-aminopropyltriethoxysilane and 15.0 g (56 mmol) 1-(2-acryloyloxyethyloxycarbonyl)-1-methoxycarbonyl-1-methoxycarbonyl-2-vinylcyclopropane in 20 ml dichloromethane was stirred at room temperature. After 14 days the solvent was distilled off in vacuo. 19.2 g (91% yield) of a clear, viscous liquid remained.

$^1$H-NMR (CDCl$_3$): 0.56 (t, 2H, SiCH$_2$), 1.22 (t, 9H, CH$_3$), 1.50 (m, 2H, CH$_2$), 1.58–1.76 (m, 4H, cyclopropyl-CH$_2$), 2.48 (m, 6H, NCH$_2$), 2.61 (m, 2H, cyclopropyl-CH), 2.78 (t, 4H, OCCH$_2$), 3.74 (s, 6H, OCH$_3$), 3.82 (q, 6H, OCH$_2$), 4.28 (m, 8H, OCH$_2$) and 5.14–5.77 (m, 6H, CH=CH$_2$) ppm.

IR (film): 2974, 1737 and 1645 cm$^{-1}$.

EXAMPLE 8

Product of addition of 3-mercaptopropyltriethoxysilane to 1-(2-acryloyloxyethyloxycarbonyl)-1-methoxycarbonyl-2-vinylcyclopropane

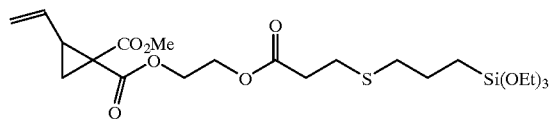

A mixture of 29.0 g (0.1 mol) 1-(2-acryloyloxyethyloxycarbonyl)-1-methoxycarbonyl-2-vinylcyclopropane, 24.5 g (0.1 mol) 3-mercaptopropyltriethoxysilane and 70 mg 1.8-diazabicyclo[5.4.0]undec-7-en (DBU) in 60 ml acetonitrile was stirred at room temperature for 3 days. After removal of solvent in vacuo, 50 g (93 % yield) of a clear, viscous liquid remained.

$^1$H-NMR (CDCl$_3$): 0.73 (t, 2H, SiCH$_2$), 1.24 (s, 12H, CH$_3$), 1.58–1.74 (m, 2H, cyclopropyl-CH$_2$ and 2H, CH$_2$), 2.52–2.79 (m, 6H, SCH$_2$, OCH and cyclopropyl-CH), 3.74 (s, 3H, OCH$_3$), 3.82 (q, 6H, OCH$_2$), 4.32 (m, 4H, OCH$_2$) and 5.13–5.84 (m, 3H, CH=CH$_2$) ppm.

IR film: 2974, 1738 and 1652 cm$^{-1}$.

EXAMPLE 9

Synthesis of 1-methoxycarbonyl-2-vinylcyclopropane-1-carboxylic acid-[2-hydroxy-3-(3-trimethoxysilylpropoxy)propyl]ester

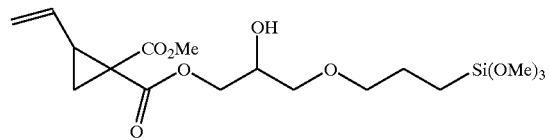

A mixture of 10.0 g (58 mmol) 1-methoxycarbonyl-2-vinylcyclopropane carboxylic acid, 14.0 g trimethoxysilylpropylglycidyl-ether and 100 mg lithium perchlorate in 20 ml dichloromethane were stirred at room temperature for 15 days. After removal of solvent in vacuo, 20 g (83% yield) of a clear, yellow viscous liquid remained.

$^1$H-NMR (CDCl$_3$): 0.68 (br, 2H, SiCH$_2$), 1.73 (br, 2H, CH$_2$), 1.98–2.15 (m, 2H, cyclopropyl—CH$_2$), 2.61 (m, 1H, cyclopropyl—CH), 3.40–3.54 (m, 5H, OH—CH—CH$_2$OCH$_2$), 3.57 (s, 9H, OCH$_3$), 3.75 (d, 2H, OCH$_2$), 3.83 (s, 3H, OCH$_3$) and 5.24–5.63 (m, 3H, CH=CH$_2$) ppm.

IR (film): 3626, 2972, 1736 and 1645 cm$^{-1}$.

EXAMPLE 10

Synthesis of 2-vinylcyclopropane-1,1-dicarboxylic acid-[N,N'-bis(3-triethoxysilylpropyl)]-amide

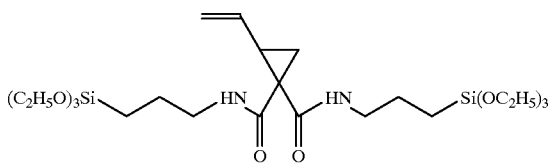

A mixture of 10.0 g (65 mmol) 2-vinylcyclopropane-1,1-dicarboxylic acid, 31.7 g (130 mmol) 3-isocyanatopropyltriethoxysilane and 40 mg dibutyltindilaurate in 100 ml anhydrous acetone were stirred at room temperature for 4 days. After no more isocyanate was detectable using IR-spectroscopy, the mixture was filtered and volatile components were removed in vacuo. 26.5 g (72% yield) of a dark oil remained.

$^1$H-NMR (CDCl$_3$): 0.62 (br, 4H, SiCH$_2$), 1.24 (t, 18H, CH$_3$), 1.60 (br, 4H, CH$_2$), 2.05–2.19 (m, 2H, cyclopropyl—CH$_2$), 2.77 (m, 1H, cyclopropyl—CH), 3.14 (t, 4H, NCH$_2$), 3.76 (s, 12H, OCH$_2$) and 5.22–5.89 (m, 3H, CH=CH$_2$) ppm.

IR (film): 3346, 2977, 1716 and 1362 cm$^{-1}$.

EXAMPLE 11

Hydrolytic condensation of 1-methoxycarbonyl-1-[(3-triethoxysilyl)propylaminocarbonyl)]-2-vinylcyclopropane (4)

100 mmol of silane (4) were dissolved in 35 ml anhydrous tetrahydrofuran (THF). The hydrolysis of the silane was accomplished by addition of 300 mmol water in form of an aqueous 0.1 N NH$_4$F solution. After stirring at room temperature for 22 hours, the volatile components were removed in vacuo. The obtained viscous resin was dissolved in 30 ml THF and 100 mmol collidine as base and 100 mmol trimethylchlorosilane (TMCS) were added under cooling to silylate remaining Si—OH groups. To complete the reaction the mixture was stirred at room temperature for about 12 hours and then the formed precipitate was separated by filtration. Before removing volatile components in vacuo, 20 mmol urethanedimethacrylate UDMA (Ivoclar, product of addition of 2 mol 2-hydroxyethylmethacrylate to 1 mol 2,2,4-trimethylhexamethylenediisocyanate) were added as a diluent to the mixture. After removal of volatile components in vacuo, a viscous resin ($\eta$=45 Pas (23° C.)) was obtained. After addition of the photoinitiator Lucirin TPO (BASF AG, 0.8 wt. %), test specimens were formed according to ISO-standard 4049 (1988) in order to examine the properties and the test specimens were cured by irradiating ith light of a wave length from 400 to 500 nm (2×3 minutes) using the dental light source Spectramat (Vivadent). It was found that the shrinkage upon polymerization was only 4.5 vol. %. Subsequently, the bending strength was determined to be 29 MPa. By means of differential scanning calorimetry (DSC) a glass transition temperature T$_g$ of 90° C. was determined. In view of these properties the material was useful as a light-curing coating or a light-curing dental material.

EXAMPLE 12

Hydrolytic condensation of 1-methoxycarbonyl-1-[(3-triethoxysilyl)propylaminocarbonyl)]-2-vinylcyclopropane (4) and co-condensation with Zr (OPr)$_4$ 100mmol of the silane (4) were dissolved in 15 ml anhydrous ethanol. The pre-hydrolysis of the silane was accomplished by additon of 150 mmol water in form of an aqueous 0.1 N NH$_4$F solution. After stirring at room temperature for 2 hours, 10 mmol of a prepared Zr(OR)-complex was added. For producing the Zr(OR)-complex 100 mmol Zr(OPr)$_4$ (80% in propanol) were mixed with 100 mmol 2-vinylcyclopropane-1,1-dicarboxylic acid monoethylester under cooling with ice, and the mixture was subsequently stirred at room temperature for 2 hours. Then, the mixture of pre-hydrolysate and Zr(OR)-complex was stirred at room temperature for further 6 hours. Before removing volatile components in vacuo, 20 mmol 1,1,1-tris-[(2-vinylcyclopropane-1-carboxylic acid methylester-1-carbonyloxy)methyl]propane and 30 mmol 2-vinylcyclopropane-1,1-dicarboxylic acid methylester as cross-linker and diluent were added to the mixture. After removing volatile components in vacuo, a viscous resin ($\eta$=46 Pas (23° C.)) was obtained which, after addition of a radical photoinitiator in accordance with Example 11, could be used as component for a light-curing coating or a light-curing dental material.

EXAMPLE 13

Hydroxytic condensation of 1-methoxycarbonyl-1-[(3-triethoxysilyl)propylaminocarbonyl)]-2-vinylcyclopropane (4) and co-condensation with tetraethoxysilane 100 mmol tetraethoxysilane (TEOS) were dissolved in 30 ml anhydrous ethanol. The pre-hydrolysis of the TEOS was effected by addition of 150 mmol water in form of aqueous 0.1 N hydrochloric acid. After stirring at room temperature for 15 minutes, 25 mmol of the silane (4) were added to the pre-hydrolysate, and 37.5 mmol water were then added in form of 0.1 N hydrochloric acid to effect hydrolysis. After stirring at room temperature for 72 hours, volatile components were removed in vacuo and a viscous resin formed which, after addition of a radical photoinitiator in accordance with Example 11, could be used as component for a light-curing coating or a light-curing dental material.

EXAMPLE 14

Hydrolytic condensation of the adduct (6) of Example 3

100mmol of silane (6) were dissolved in 55 ml anhydrous THF. The hydrolysis of the silane was effected by addition of 300 mmol water in form of aqueous 0.1 N hydrochloric acid. After stirring at room temperature for 25 hours, the volatile components were removed in vacuo. The formed visous resin was dissolved in 50 ml THF and 100 mmol collidine as a base and 100 mmol TMCS were added under cooling to silylate remaining Si—OH-groups. To complete the reaction, the mixture was stirred at room temperature for about 12 hours and then the formed precipitate of collidine hydrochloride was separated by filtration. Before removing volatile components in vacuo, 30 mmol urethanedimethacrylate UDMA were added to the mixture as diluent. After removing volatile components in vacuo, a viscous resin was obtained ($\eta$=65 Pas (23° C.)). After addition of the photoinitiator lucirin TPO (0.8 wt. %) the resin was cured in an analogous manner as in Example 11 and the shrinkage upon polymerization was only 3.7 vol. % and the T$_g$ was 68° C.

EXAMPLE 15

Hydrolytic condensation of the adduct (6) of Example 3 and co-condensation with Zr (OPr)$_4$ 100 mmol of the silane (6) were dissolved in 25 ml anhydrous ethanol. The pre-hydroxlysis of the silane was effected by addition of 150 mmol water in form of an aqueous 0.1 N NH$_4$F solution. After stirring at room temperature for 2 hours, 10 mmol of the prepared Zr(OR)-complex were added. In order to prepare the Zr(OR)-complex, 100 mmol Zr(OPr)$_4$ (80% in propanol) were mixed with 100 mmol 2-vinylcyclopropane-1,1-dicarboxylic acid monoethylester under cooling with ice and subsequently the mixture was stirred at room temperature for 2 hours. The mixture of prehydrolysate and Zr-complex was then stirred at room temperature for additional 15 hours. Before removing volatile components in vacuo, 20 mmol 1,1, 1-tris-[(2-vinylcyclopropane-1,1-dicarboxylic acid methylester-1-carbonyloxy)methyl]propane and 30 mmol 2-vinylcyclopropane-1,1,-dicarboxylic acid methylester as cross-linker and diluent were added to the mixture. After removing volatile components in vacuo, a viscous resin (η=120 Pas (23° C.)) was obtained which, after addition of a radical photoinitiator analogous to Example 11, was useful as component for a light-curing coating or a light-curing dental material.

EXAMPLE 16

Hydrolytic condensation of adduct (6) of Example 3 and co-condensation with tetraethoxysilane 100 mmol TEOS were dissolved in 35 mol anhydrous ethanol. The pre-hydrolysis of the TEOS was accomplished by addition of 150 mmol water in form of 0.1 N hydrochloric acid. After stirring at room temperature for 15 minutes,, 25 mmol of silane (6) were added to the pre-hydrolysate. Then, 37.5 mmol water in form of 0.1 N hydrochloric acid were added to effect hydrolysis. After stirring at room temperature for 72 hours, volatile components were removed in vacuo and a viscous resin formed which, after addition of photoinitiator, gave a light-curing resin useful as component of a dental material.

EXAMPLE 17

Hydrolytic condensation of the di-adduct (7) of Example 4 and co-condensation with diphenyldimethoxysilane 100 mmol of silane (7) and 100 mmol diphenyldimethoxysilane (DPhDMS) were dissolved in 30 ml anhydrous THF. The hydrolysis of the silanes was accomplished by addition of 500 mmol water in form of 0.1 N hydrochloric acid. After stirring at room temperature for 36 hours, volatile components were removed in vacuo and a viscous resin formed which, after addition of radial initiator, was useful as component for a light-curing dental material.

EXAMPLE 18

Hydrolytic condensation of the silane of Example 7

100 mmol of silane according to Example 7 were dissolved in 75 ml anhydrous THF. The hydrolysis of the silane was accomplished by addition of 300 mmol water in form of an aqueous 0.1 N NH$_4$F solution. After stirring at room temperature for 22 hours, volatile components were removed in vacuo. The so-produced viscous resin was dissolved in 60 ml THF and 100 mmol collidine as base and 100 mmol TMCS were added under cooling in order to silylate still present Si—OH groups. The mixture was stirred at room temperature for about 12 hours in order to complete the reaction and then the formed precipitate of collidine hydrochloride was separated by filtration. Before removing volatile components in vacuo, 30 mmol urethane dimethacrylate UDMA were added as diluent to the mixture. After removing volatile components in vacuo, a viscous resin (η=80 Pas (23° C.)) was obtained. After addition of photoinitiator lucirin TPO (0.8 wt. %), the resin was cured in a manner analogous to Example 11 and the bending strength of the obtained material was 40.5 MPa, the shrinkage upon polymerization was only 3.9 vol. % and the T$_g$ was 76° C.

EXAMPLE 19

Hydrolytic condensation of silane of Example 7 and co-condensation with tetraethoxysilane 25 mmol TEOS were dissolved in 45 ml anhydrous ethanol. The pre-hydrolysis of the TEOS was accomplished by addition of 37.5 mmol water in form of 0.1 N hydrochloric acid. After stirring at room temperature for 15 minutes, 100 mmol of the silane of Example 7 were added to the pre-hydrolysate, and then 150 mmol water in form of 0.1 N hydrochloric acid were added to effect hydrolysis. After stirring at room temperature for 72 hours, the volatile components were removed in vacuo, whereupon a viscous resin formed which, after addition of radical initiator, was useful as component for a light-curing coating or a light-curing dental material.

EXAMPLE 20

Hydrolytic condensation of silane of Example 8

100 mmol of the silane of Example 8 were dissolved in 30 ml anhydrous THF. The hydrolysis of the silane was accomplished by addition of 300 mmol water in form of an aqueous 0.1 N NH$_4$F solution. After stirring at room temperature for 36 hours, the volatile components were removed in vacuo and a viscous resin formed which, after addition of radical initiator, was useful as component for a light-curing dental material.

EXAMPLE 21

Hydrolytic condensation of silane of Example 8 and co-condensation with Al(OBu)$_3$ 100 mmol of silane of Example 8 were dissolved in 25 ml anhydrous THF. The pre-hydrolysis of the silane was accomplished by addition of 150 mmol water in form of an aqueous 0.1 N NH$_4$F solution. After stirring at room temperature for 20 hours, 10 mmol of prepared Al(OR) complex were added. In order to prepare the Al(OR) complex, 100 mmol Al(OBu)$_3$ were dissolved in 55 ml THF and mixed with 200 mmol 2-vinylcyclopropane-1,1-dicarboxylic acid monoethylester under cooling with ice, and subsequently the mixture was stirred at room temperature for 2 hours. After stirring at room temperature for 72 hours, the volatile components were removed in vacuo and a viscous resin formed which, after addition of a radical initiator, was useful as component for a light-curing dental material.

We claim:

1. A hydrolysable and polymerizable vinylcyclopropane silane of the general formula (I) and stereoisomers thereof

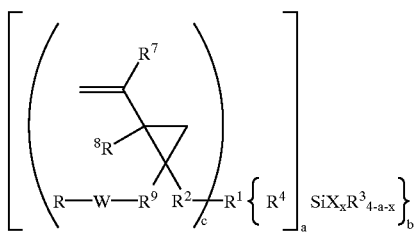

(I)

in which the variables $R, R^1, R^2, R^3, R^4, R^5, R^6, R^7, R^8, R^9, W, X, Y, a, b, c, x$, unless otherwise stated, independently of one another have the following meanings:

R=hydrogen, substituted or unsubstituted $C_1$ to $C_{12}$ alkyl, $C_7$ to $C_{15}$ alkylaryl or $C_6$ to $C_{14}$ aryl or $R^3{}_{3-x}X_xSi$—$R_4$—$R_1$—$R_2$—;

$R^1$=missing or represents substituted or unsubstituted $C_1$ to $C_{18}$ alkylene, $C_6$ to $C_{18}$ arylene. $C_7$ to $C_{18}$ alklylenearylene or arylenealkylene radicals, these radicals bein,, able to be interrupted by or terminated with at least one group selected from ether, thioether, ester, carbonyl, amide and urethane groups;

$R^2$=missing or represents substituted or unsubstituted $C_1$ to $C_{18}$ alkylene, $C_6$ to $C_{18}$ arylene, $C_7$ to $C_{18}$ alkylenearylene or $C_7$ to $C_{18}$ arylenealkylene radicals, these radicals being able to be interrupted by or terminated with at least one group selected from ether, thioether, ester, thioester, carbonyl, amide and urethane groups;

$R^3$=missing or represents substituted or unsubstituted $C_1$ to $C_{18}$ alkly, $C_2$ to $C_{18}$alkenyl, $C_6$ to $C_{18}$ aryl, $C_7$ to $C_{18}$alklylaryl or $C_7$ to $C_{18}$arylalkyl, these radicals being able to be interrupted by at least one group selected from ether, thioether, ester, carbonyl, amide and urethane groups;

$R^4$=missing or represents substituted or unsubstituted —$CHR^6$—$CHR^6$—,—$CHR^6$—$CHR^6$—$S$—$R^5$,—$S$—$R^5$—,—$Y$—$CO$—$NH$—$R^5$— or —$CO$—$O$—$R^5$—;

$R^5$=substituted or unsubstituted $C_1$ to $C_{18}$ alkylene, $C_6$ to $C_{18}$ arylene, $C_6$ to $C_{18}$ alkylenearylene or $C_6$ to $C_{18}$ arylenealkylene, these radicals being able to be interrupted by at least one group selected from ether, thioether, ester, carbonyl, amide and urethane groups:

$R^6$=hydrogen, or substituted or unsubstituted $C_1$ to $C_{18}$ alkyl or $C_6$ to $C_{10}$ aryl;

$R^7$=hydrogen, or substituted or unsubstituted $C_1$ to $C_{10}$ alkyl or halogen or hydroxy;

$R^8$=Hydrogen or substituted or unsubstituted $C_1$ to $C_{10}$ alkyl;

$R^9$=missing or represents substituted or unsubstituted $C_1$ to $C_{10}$ alkylene;

W=missing or represents carbonyl, ester, ether, thioether, amide or urethane groups;

X=a hydrolysable group, namely halogen, hydroxy, alkoxy or acyloxy;

Y=O or S;

a=1, 2 or 3;

b=1, 2 or 3;

c=1 to 6; and x=1, 2 or 3; and with the proviso that (i) a+x=2,3 or 4 and (ii) a and/or b=1.

2. A vinylcyclopropane silane according to claim 1, wherein at least one of the variables of formula (I), unless othernise stated, independently of the other variables, has the following meaning:

R=$C_1$ to $C_5$ alkyl, benzyl or phenyl or $R^3{}_{3-x}X_xSi$—$R_4$—$R_1$—$R_2$—;

$R^1$=$C_1$ to $C_8$ alkylene radical, this radical being able to be interrupted by at least one group selected from ether, thioether, ester and urethane groups;

$R^2$=missing or represents ($C_1$ to $C_8$ alkylene radical, this radical being able to be interrupted by or terminated with at least one group selected from ether, thioether, ester, thioester, carbonyl, amide and urethane groups;

$R^3$=missing, or represents methyl, ethyl or phenyl;

$R^4$=missing or represents —$CHR^6$—$CHR^6$—, —$S$—$R^5$—, —$Y$—$CO$—$NH$—$R^5$— or —$CO$—$O$—$R^5$—;

$R^5$=$C_1$ to $C_8$ alkylene, these radicals being able to be interrupted by at least one group selected from ether, thioether, ester, carbonyl, amide and urethane groups:

$R^6$=hydrogen or $C_1$ to $C_5$ alkyl;

$R^7$=hdrogen or $C_1$ to $C_5$ alkyl;

$R^8$=hydrogen or $C_1$ to $C_5$ alkyl;

$R^9$=missing or represents $C_1$ to $C_3$ alkylene;

W=ester, amide or urethane group;

X=methoxy, ethoxy or chloro;

Y=O or S;

a=1;

b=1;

c=1 to 6;

x=2 or 3; and/or a+x=3.

3. A vinylcyclopropane silane according to claim 1, wherein at least one of the variables a, b or c is 1.

4. A polymerizable silicic acid condensate of the vinylcyclopropane silane according to claim 1.

5. A polymer comprising the vinylcyclopropane silane according to claim 1.

6. A composition comprisins the vinylcyclopropane silane according to claim 1.

7. A polymer comprising the silicic acid condensate according to claim 4.

8. A composition comprising the silicic acid condensate according to claim 4.

9. A dental material comprising the vinylcyclopropane silane according to claim 1.

10. A dental material comprising the silicic acid condensate according to claim 4.

11. A dental material comprising the polymer of claim 7.

12. A dental material comprising the polymer of claim 9.

13. A method of producing a silicic acid condensate comprising:

providing the vinylcyclopropane silane according to claim 1 and reacting the vinylcyclopropane silane under conditions effective to produce the silicic acid condensate.

14. A composition according to claim 8, further comprising a diluent monomer.

15. A composition according to claim 14, further comprising a polymerization initiator.

16. A composition according to claim 15, further comprising an additive.

17. A composition according to claim 16, wherein the additive is a filler.

18. A composition according to claim 17, wherein the composition comprises 5 to 90 wt. % of the silicic acid condensate, up to 80 wt. % of the diluent monomer, 0.1 to 5 wt. % of the polymerization initiator, and up to 90 wt. % of the filler.

19. A method of producing a dental material comprising:

providing the vinylcyclopropane silane according to claim 1 and polymerizing the vinylcyclopropane silane under conditions effective to produce the dental material.

20. A method of producing a dental material comprising:

providing the silicic acid condensate according to claim 4 and polymerizing the silicic acid condensate under conditions effective to produce the dental material.

* * * * *